United States Patent [19]
Bron

[11] Patent Number: 5,421,363
[45] Date of Patent: Jun. 6, 1995

[54] ADJUSTABLE RATE FLOW REGULATOR

[76] Inventor: Dan Bron, 39/47 Soroka Street, Haifa 34759, Israel

[21] Appl. No.: 212,784

[22] Filed: Mar. 15, 1994

[30] Foreign Application Priority Data

Mar. 16, 1993 [IL] Israel .................................... 107071

[51] Int. Cl.⁶ .............................................. G05D 7/01
[52] U.S. Cl. .................................................... 137/501
[58] Field of Search .............................. 137/501, 504

[56] References Cited

U.S. PATENT DOCUMENTS

| | | | |
|---|---|---|---|
| 4,343,305 | 8/1982 | Bron | 137/501 x |
| 5,101,854 | 4/1992 | Bron | 137/501 |

FOREIGN PATENT DOCUMENTS 0270500 6/1988 European Pat. Off. .
0373564 6/1990 European Pat. Off. .

Primary Examiner—Robert G. Nilson
Attorney, Agent, or Firm—Larson and Taylor

[57] ABSTRACT

An adjustable-rate flow regulator, including a split housing having an inverted-cup-shaped upper half connectable to a source of liquid to be dispensed, the upper half having a wall and a downward-facing bottom surface provided with an inlet port, and a lower half rotatably engaging the upper half, the lower half having a neck portion of reduced diameter and a recessed upper face having, at the bottom thereof, a control port leading to the consumer of the liquid. The regulator further includes an elastically deformable diaphragm seated on an annular step in the recess and defining with the bottom surface of the upper housing half a first chamber, and with the bottom of the recess in the lower housing half, a second chamber, and a tubular flow attenuator made of an elastomer, rotatably seated on, and fluid-tightly surrounding, the neck portion of the lower housing half, but non-rotatable relative to the upper housing half. The inner wall surface of the tubular flow attenuator defines in conjunction with the neck portion a system of flow-attenuating ducts for the liquid, the flow-attenuating effect of which ducts can be varied to adjust the rate of flow, through the regulator, of the liquid.

12 Claims, 3 Drawing Sheets 5,421,363

ADJUSTABLE RATE FLOW REGULATOR

The present invention relates to a flow regulator, more particularly to an adjustable-rate flow regulator to be used in an infusion set.

In U.S. Pat. No. 3,343,305, there is described an adjustable-rate, constant-output infusion set with, however, a rather limited accuracy of the flow rates obtainable.

It is one of the objects of the present invention to provide such a flow regulator with a greatly enhanced accuracy and improved repeatability.

According to the present invention, such a regulator is made possible by providing an adjustable-rate flow regulator, comprising a split housing having an inverted-cup-shaped upper half connectable to a source of liquid to be dispensed, said upper half having a wall and a downward-facing bottom surface provided with an inlet port, and a lower half rotatably engaging said upper half, said lower half having a neck portion of reduced diameter and a recessed upper face comprising, at the bottom thereof, a control port leading to the consumer of said liquid, an elastically deformable diaphragm seated on an annular step in said recess and defining with the bottom surface of said upper housing half a first chamber, and with the bottom of said recess in said lower housing half, a second chamber, and a tubular flow attenuator made of an elastomer, rotatably seated on, and fluid-tightly surrounding, said neck portion of said lower housing half, but non-rotatable relative to said upper housing half, characterized in that the inner wall surface of said tubular flow attentuator defines in conjunction with said neck portion a system of flow-attenuating ducts for said liquid, the flow-attenuating effect of which ducts can be varied to adjust the rate of flow, through said regulator, of said liquid.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invetion may be embodied in practice.

Figure 1:
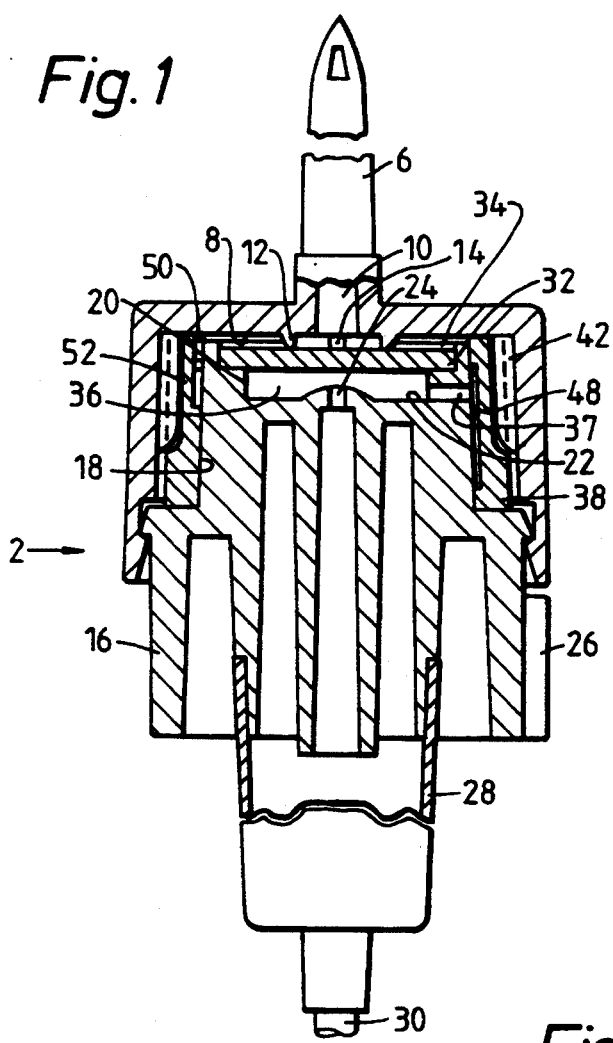
FIG. 1 is a partial cross-sectional view of the flow regulator according to the invention as used in an infusion set.

Referring now to the drawings, there is seen in FIG. 1 a split housing 2 having an inverted-cup-shaped upper half 4 and connectable to an infusion-liquid bag or bottle (not shown) by means of a pointed snout 6.

The downward-facing bottom surface 8 of the upper half 4 is provided with an inlet port 10 surrounded by a rim which, at at least one point, has a slot or notch 14, the purpose of which will be explained further below.

The lower housing half 16 of the split housing 2 snap-locks into an appropriately shaped groove in the substantially cylindrical wall of the upper half 4 and is thus constrained to move only (i.e., has one degree of freedom) in rotation relative to that upper half 4. The lower half 16 has a neck portion 18 of a reduced diameter and a stepped recess 20 in its upper face, the bottom 22 of which recess 20 is provided with a slightly raised control port 24.

The lower portion of the lower housing half 16 is seen to carry at least one rib 26 which serves as an index marker to read off, on a scale (not shown), provided on the upper half 4, the degree of relative rotation.

Also seen in FIG. 1 is a drip chamber 28 fixedly attached to the lower housing half 16, with a flexible tubing 30 leading to the patient.

Freely seated on a step in the above-mentioned recess 20, there is seen an elastically deformable diaphragm 32 which, with the bottom surface 8 of the upper housing half 4 defines a first chamber 34, and with the bottom 22 of the recess 20, a second chamber 36. Liquid access to this second chamber 36 is through a passage 37.

Figure 2:
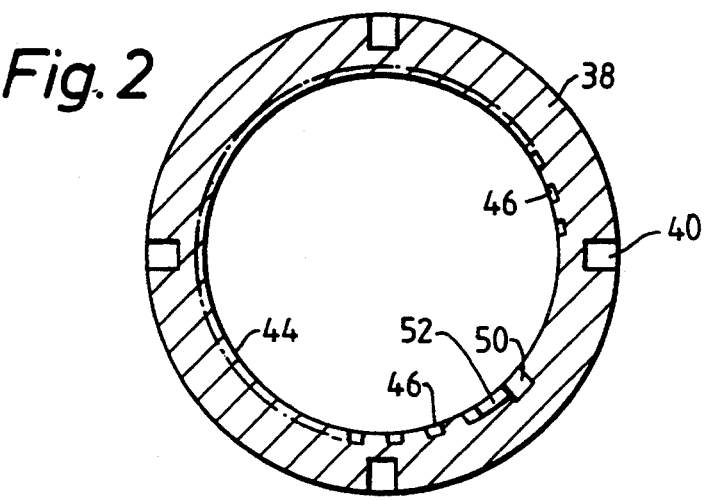
FIG. 2 is a view, in cross section along plane II—II in FIG. 3, of the tubular flow attenuator.

The flow attenuator 38, as can be seen from FIGS. 1 and 2, is tubular and is a sliding fit on the neck portion 18 of the lower housing half 16. It is made of an elastomer and its height is such as to seal off the first chamber 36 from the rest of the inside space of the upper housing half 4.

FIG. 2 shows four slots 40 extending along about two-thirds of the height of the flow attenuator 38. In these slots 40 engage four ribs integral with the inside wall surface of the upper housing half 4, preventing a relative rotation between the flow attenuator 38 and the upper housing half 4. In other words, whenever, (for a purpose to be explained further below), the upper housing half 4 is rotated relative to the lower housing half 16, the flow attenuator 38 is dragged along by the upper housing half 4.

Figure 3:
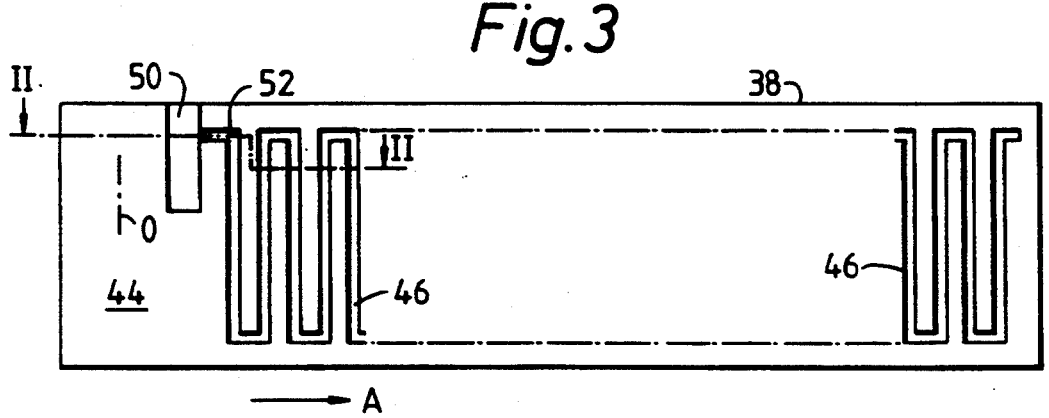
FIG. 3 is a developed view showing a first version of the meander-type labyrinth provided on the inside wall surface of the tubular flow attenuator.

The inside wall surface 44, a development of which is shown in FIG. 3, carries a pattern of grooves 46 in the form of a meander-type labyrinth which, in conjunction with the neck portion 18 of the lower housing half 16, constitutes a flow-attenuating system of ducts 48 (FIG. 1). While the "limbs" of the grooves 46, i.e, the distance between two succesive points of directional reversal, is uniform, the depth of the grooves 46, that is, the free flow cross section of the ducts 48, gradually decreases in direction of arrow A, i.e., in direction of flow. This is also evident from FIG. 2, which shows a few grooves 46 at the beginning and at the end of the system. The grooves 46 are shown to a greatly enlarged scale, the true size of their cross-sectional area being of an order of magnitude of 0.1 mm$^2$.

Obviously, for narrow ranges of flow rates, the depth of the grooves 46 could be kept uniform.

Seen is also a feeding groove 50 (see also FIG. 1) through which the liquid, coming from the first chamber 34, enters the labyrinth through the short horizontal groove 52.

Figure 4:
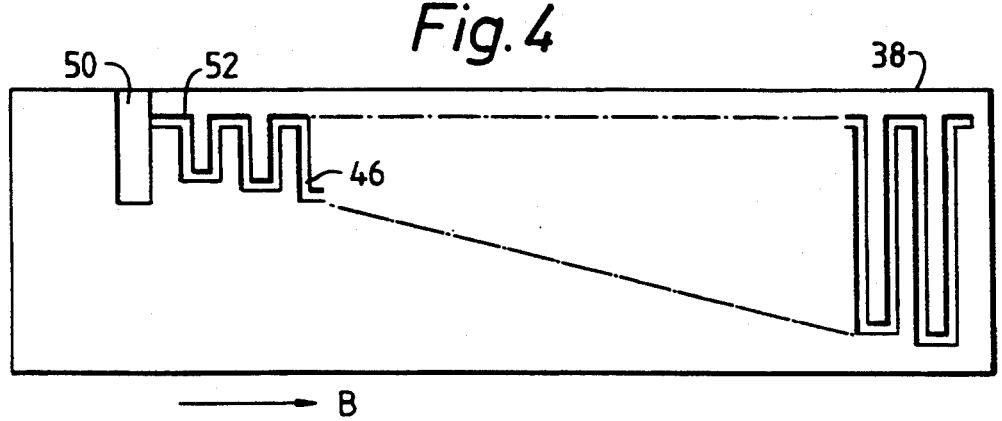
FIG. 4 is a similar view of a second version of this labyrinth.

A variant of the flow attenuator 38 is shown in FIG. 4, in which the depth of the grooves 46 is constant, and so is, obviously, the cross sectional area of the ducts 48. However, as can be seen in FIG. 4, the length of the "limbs" is gradually increasing in direction of liquid flow, i.e., in direction of arrow B.

The principles of the use of an elastic diaphragm in flow regulation, i.e., in the obtaining of constant flow in spite of changes in the pressure head are well-known today (as described, e.g., in U.S. Pat. No. 4,343,305) and need not be repeated here. However, the way in which the flow or dripping rate can be adjusted or set within any elected range, for example, a range of 3–60 ml/hr, requires some explanation.

As due to the regulator function of the present device, the pressure drop across the diaphragm is constant, the flow rate depends only on the resistance encountered by the liquid during its passage through the flow-attenuating labyrinth, which resistance is, obviously, a function of the length (and cross-sectional area) of the labyrinth system to be passed by the liquid on its way from the first chamber 34 via the feeding groove 50 into the system of the ducts 48 and thence through the passage 37 into the second chamber 36.

This length can be varied by varying the angular distance between the feeding groove 50 in the flow attenuator 38 and the passage 37 through the wall of the recess 20 in the neck portion 18 of the lower housing half 16. This angular distance can be varied by producing a relative rotation between the upper and the lower housing halves 4,16, remembering that, due to the ribs 42 of the upper half 4 engaging in the flow attenuator 38, the latter is coupled to the upper housing half 4 and takes part in every rotation of the upper half 4 relative to the lower half 16.

Clearly, the shorter the active length of the labyrinth, the higher the flow or dripping rate. A scale is advantageously provided on the lower edge of the upper housing half 4, with the already mentioned rib 26 serving as index.

Apart from the active range, such a scale would also include two special markings: "P" for Priming, when the passage 37 is brought into coincidence with the feeding groove 50. At this setting, the labyrinth is neutralized and the infusion set can be rapidly "primed", i.e., filled with liquid. The second marking would be "0", when the passage 37 is brought to the region "0" in FIG. 3, which shuts off any flow in the system.

Figure 5:
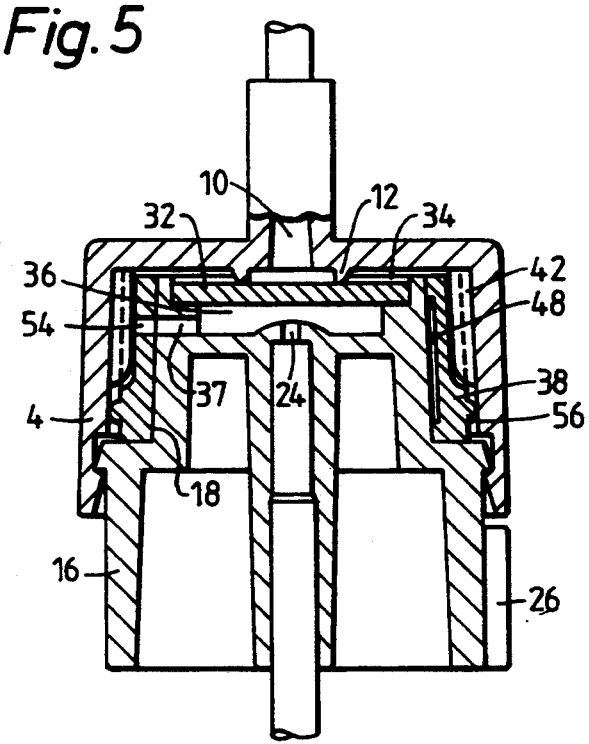
FIG. 5 is a partial cross-sectional view of an in-line embodiment of the flow regulator.

FIG. 5 illustrates an in-line flow regulator arranged below a drip chamber (not shown). In this embodiment, the labyrinth is supplied not through a feeding groove 50 located between the neck portion 18 and the inside wall 44 of the flow attenuator 38, but through an opening 54 in the latter. The regulator is here shown in the "P" position. As the liquid now arrives from the outside wall of the attenuator 38, the latter is of a lesser height than in the embodiment of FIG. 1, to permit the liquid from the first chamber 34 to reach the opening 54. Sealing off the upper housing half 4 is now effected by a peripheral bead 56, which sealingly contacts the inside wall surface of the upper housing half 4. In this embodiment the pressure obviously apears also on the outer side of the attenuator 38, thus ensuring a tight contact between the latter and the neck portion 18 and preventing liquid escape from the labyrinth also at higher pressures.

Since the drip chamber, as explained, is arranged above the flow regulator, there is no need for the notch 14 in the rim 12 for the venting of air. The rim 12, in conjunction with the diaphragm 32 can now work as a nonreturn valve, preventing blood from being drawn from the patient when the infusion-liquid bag accidentally falls to a level lower than that of the patient.

Figure 6:
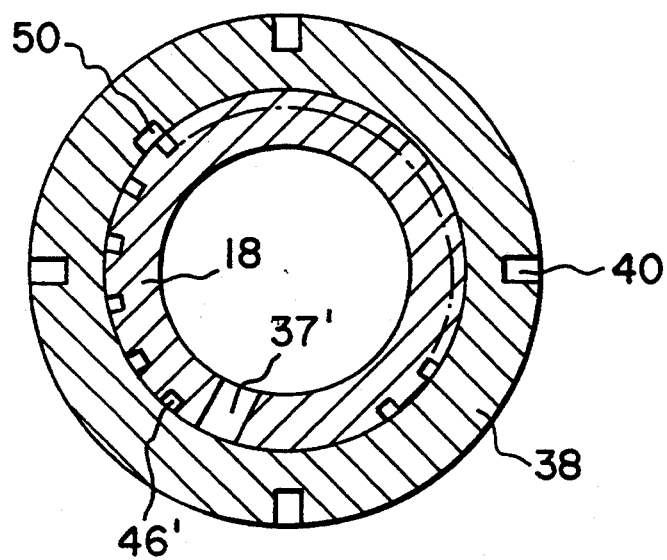
FIG. 6 is a cross-sectional view, similar to that of FIG. 2, with the pattern of grooves being provided in the outer surface of the neck portion.

The labyrinth could obviously be of a different shape and the grooves 46' forming the latter could be provided in the neck portion 18 of the lower housing half 16 as shown in FIG. 6, rather than in the tubular flow attenuator 38 as shown in FIG. 2. Furthermore, it would also be possible to gradually change the cross-sectional area of the grooves 46 of the attenuator of FIG. 4. The passageway 37' in FIG. 6 has the same function as the passageway 37 in FIG. 1.

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An adjustable-rate flow regulator, comprising:
   a split housing having an inverted-cup-shaped upper half connectable to a source of liquid to be dispensed, said upper half having a wall and a downward-facing bottom surface provided with an inlet port, and a lower half rotatably engaging said upper half, said lower half having a neck portion of reduced diameter and a recessed upper face comprising, at the bottom thereof, a control port leading to the consumer of said liquid;
   an elastically deformable diaphragm seated on an annular step in said recess and defining with the bottom surface of said upper housing half a first chamber, and with the bottom of said recess in said lower housing half, a second chamber, and
   a tubular flow attenuator made of an elastomer, rotatably seated on, and fluid-tightly surrounding, said neck portion of said lower housing half, but non-rotatable relative to said upper housing half,
   characterized in that the inner wall surface of said tubular flow attenuator defines in conjunction with said neck portion a system of flow-attenuating ducts for said liquid, the flow-attenuating effect of which ducts can be varied to adjust the rate of flow, through said regulator, of said liquid.

2. The flow regulator as claimed in claim 1, wherein said flow-attenuating ducts are produced by a system of grooves provided in the inner wall surface of said tubular flow attenuator, which grooves, in conjunction with the surface of said neck portion, are turned into ducts.

3. The flow regulator as claimed in claim 1, wherein said flow-attenuating ducts are produced by a system of grooves provided in the outer surface of said neck portion, which grooves, in conjunction with said tubular elastomer rotatably seated on, and fluid-tightly surrounding, said neck portion, are formed into ducts.

4. The flow regulator as claimed in claim 1, wherein said ducts form a labyrinth comprised of a plurality of meanders, the distance between successive points of reversal of said meanders being constant.

5. The flow regulator as claimed in claim 1, wherein the free cross-section of said ducts decreases gradually in the direction of liquid flow.

6. The flow regulator as claimed in claim 1, wherein the free cross-section of said ducts remains constant along their entire extent.

7. The flow regulator as claimed in claim 1, wherein said ducts form a labyrinth comprised of a plurality of meanders, the distance between successive points of reversal of said meanders increasing gradually in a direction of fluid flow.

8. The flow regulator as claimed in claim 1, wherein the outer wall surface of said tubular flow attenuator is provided with at least one slot in an axial direction, in which slot engages an axially oriented rib integral with the inside wall surface of said upper housing half.

9. The flow regulator as claimed in claim 1, wherein, close to its lower edge, the outer wall surface of said tubular flow attentuator is provided with a peripheral bead sealingly contacting the inside wall surface of said upper housing half.

10. The flow regulator as claimed in claim 1, wherein said inlet port is surrounded by a rim.

11. The flow regulator as claimed in claim 10, wherein said rim is provided with at least one notch to enable venting of air from a drip chamber via said first chamber and said inlet port, into said source.

12. An adjustable-rate flow regulator, comprising:
a split housing having a first half connectable to a source of liquid to be dispensed and being provided with an inlet port for said liquid, a second half rotatably engaging said first half and having a neck portion of reduced diameter and a recessed face, with the bottom thereof having a control port;
an elastically deformable diaphragm seated in said recess and defining with said first half a first chamber, and with said second half a second chamber; and
a tubular flow attenuator rotatably seated on, and fluid-tightly surrounding with its inner wall surface, the outer wall surface of said neck portion;
wherein the inner wall surface of said tubular flow attenuator defines in conjunction with said neck portion a system of flow-attenuating ducts for said liquid, the flow-attenuating effect of which ducts can be varied to adjust the rate of flow, through said regulator, of said liquid.

* * * * *